US009846955B2

(12) United States Patent
Lee et al.

(10) Patent No.: US 9,846,955 B2
(45) Date of Patent: Dec. 19, 2017

(54) METHOD AND APPARATUS FOR GENERATING IMAGE THAT INDUCES EYE BLINKING OF USER, AND COMPUTER-READABLE RECORDING MEDIUM THEREFOR

(71) Applicant: Samsung Display Co., Ltd., Yongin, Gyeonggi-Do (KR)

(72) Inventors: Changhoon Lee, Yongin (KR); Ilnam Kim, Yongin (KR); Jongin Baek, Yongin (KR); Yijoon Ahn, Yongin (KR); Wonsang Park, Yongin (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 3 days.

(21) Appl. No.: 14/578,026

(22) Filed: Dec. 19, 2014

(65) Prior Publication Data

US 2016/0012622 A1   Jan. 14, 2016

(30) Foreign Application Priority Data

Jul. 8, 2014   (KR) ........................ 10-2014-0085367

(51) Int. Cl.
*G06T 11/60* (2006.01)
*A61B 3/00* (2006.01)
(Continued)

(52) U.S. Cl.
CPC ................ *G06T 11/60* (2013.01); *A61B 3/00* (2013.01); *A61B 3/113* (2013.01); *A61B 5/1103* (2013.01); *G06F 3/14* (2013.01)

(58) Field of Classification Search
None
See application file for complete search history.

(56) References Cited

U.S. PATENT DOCUMENTS 6,873,327 B1    3/2005  Edwards et al.
7,446,762 B2 *  11/2008 Hsieh ....................... G09G 5/00
                                                  345/204
(Continued)

FOREIGN PATENT DOCUMENTS

JP          8-242411 A       9/1996
JP       2000-339438 A      12/2000
(Continued)

OTHER PUBLICATIONS

Fawad Mir, "Fotowall Is Easy-To-Use Application for Creating Photo Collages," http://www.addictivetips.com/windows-tips/fotowall-is-easy-to-use-application-for-creating-photo-collages/, Dec. 28, 2011.*

(Continued)

*Primary Examiner* — Nicholas R Wilson
(74) *Attorney, Agent, or Firm* — Knobbe Martens Olson & Bear LLP (57) ABSTRACT

A method of displaying an image that induces eye blinking of a user is disclosed. In one aspect, the method includes displaying a main image in a display area of a display device and generating an auxiliary image configured to induce eye blinking of a user. The method also includes combining the main image and the auxiliary image and displaying the combined image in a first area corresponding to a portion of the display area.

14 Claims, 5 Drawing Sheets

(51) Int. Cl.
*G06F 3/14* (2006.01)
*A61B 3/113* (2006.01)
*A61B 5/11* (2006.01)

(56) References Cited

U.S. PATENT DOCUMENTS

| | | | |
|---|---|---|---|
| 7,487,529 | B1 | 2/2009 | Orlick |
| 8,634,673 | B1 * | 1/2014 | McDougal ............... G06T 5/00 382/274 |
| 2005/0220321 | A1 * | 10/2005 | Langelaar ............. G06T 1/0028 382/100 |
| 2006/0189879 | A1 | 8/2006 | Miyajima et al. |
| 2007/0268234 | A1 | 11/2007 | Wakabayashi et al. |
| 2008/0143739 | A1 * | 6/2008 | Harris ..................... G09G 5/02 345/604 |
| 2008/0259098 | A1 | 10/2008 | Zamorsky et al. |
| 2010/0058229 | A1 * | 3/2010 | Mercer ................. G06F 9/4443 715/788 |
| 2011/0298702 | A1 | 12/2011 | Sakata et al. |
| 2012/0123191 | A1 * | 5/2012 | Surenthiran ............. A61H 5/00 600/27 |
| 2013/0083215 | A1 | 4/2013 | Wisniewski |
| 2013/0141439 | A1 | 6/2013 | Kryzhanovsky et al. |
| 2013/0216204 | A1 | 8/2013 | Kulakov |
| 2015/0220157 | A1 | 8/2015 | Marggraff et al. |
| 2015/0356954 | A1 | 12/2015 | Lee et al. |
| 2016/0012622 | A1 | 1/2016 | Lee et al. |

FOREIGN PATENT DOCUMENTS

| | | | |
|---|---|---|---|
| KR | 10-1999-0048705 | A | 7/1999 |
| KR | 10-2000-0049412 | A | 8/2000 |
| KR | 10-2001-0091322 | A | 10/2001 |
| KR | 10-0434894 | B1 | 5/2004 |
| KR | 10-0641139 | B1 | 10/2006 |
| KR | 10-2009-0002306 | A | 1/2009 |
| KR | 10-2012-0124256 | A | 11/2012 |
| KR | 10-2015-0135660 | A | 12/2015 |
| WO | WO 2013/062180 | A1 | 5/2013 |
| WO | WO 2013/065900 | A1 | 10/2013 |

OTHER PUBLICATIONS

Duff et al., "Compositing Digital Images," Computer Graphics Project, Lucasfilm Ltd., ACM, 1984.*
Larry Jordan, "FCP X: Create a Luma Key," https://larryjordan.com/articles/fcpx-luma-key/, Sep. 23, 2012.*
Polatsek, Patrik, *Blink Rate Tracking of Computer User*, Bachelor Thesis, *Institute of Informatics and Software Engineering, FIIT STU Bratislava*, May 2013, 84 pages.
EyeLeo, "EyeLeo prevents eye strain," *EyeLeo.com, 2010*, retrieved from http://web.archive.org/web/20131217135652/http://eyeleo.com/, 2013, p. 1/1.
Visolve for Windows, "The assistive software for people with color blindness," retrieved from http://www.ryobi-sol.eo.jp/visolve/windows/en/, © 2013 Ryobi System Solutions, all screens (pages).
European Office Action dated Aug. 9, 2016 in European Patent Application No. 15156262.6.

* cited by examiner

METHOD AND APPARATUS FOR GENERATING IMAGE THAT INDUCES EYE BLINKING OF USER, AND COMPUTER-READABLE RECORDING MEDIUM THEREFOR

CROSS-REFERENCE TO RELATED APPLICATIONS

This application claims the benefit of Korean Patent Application No. 10-2014-0085367, filed on Jul. 8, 2014, in the Korean Intellectual Property Office, the disclosure of which is incorporated herein in its entirety by reference.

BACKGROUND

Field

The described technology generally relates to a method, apparatus, and a computer readable recording medium for displaying an inducement image that induces eye blinking of a user.

Description of the Related Technology

Dry eye syndrome is a disease that can result in sore eyes, affect the eye sensory perception, and induce a sensation of a foreign object in the eye. Eye dryness can result from insufficient tearing, excessive tear evaporation, or an imbalance of tear components.

As the use of computers or smartphones become widespread, more people are affected by the dry eye syndrome. When a person concentrates on watching a computer monitor or a TV, eye blinking is unconsciously reduced and tears quickly evaporate, and thus, causing dry eye syndrome.

SUMMARY OF CERTAIN INVENTIVE ASPECTS

One inventive aspect is a method of and apparatus for generating an image that induces eye blinking of a user and a computer readable recording medium for executing the method.

Another aspect is a method of displaying an image that induces eye blinking of a user, wherein the method is performed using a processor and includes: displaying an image in a display area; generating an image that induces eye blinking of the user based on the displayed image and an auxiliary image that is provided apart from the displayed image; and displaying the image that induces eye blinking of the user in a first area corresponding to a portion of the display area.

Another aspect is an apparatus for displaying an image that induces eye blinking of a user, which includes: a display control unit that displays an image in a display area and the image that induces eye blinking of the user in a first area corresponding to a portion of the display area; and an image generating unit that generates the image that induces eye blinking of the user based on the displayed image and an auxiliary image that is provided apart from the displayed image.

Another aspect is a non-transitory computer readable recording medium having embodied thereon a program for executing the method described above on a computer is included.

Another aspect is a method of displaying an image, the method being performed by a processor and comprising: displaying a main image in a display area of a display device; generating an auxiliary image configured to induce eye blinking of a user; combining the main image and the auxiliary image; and displaying the combined image in a first area corresponding to a portion of the display area.

In the above method, the auxiliary image is the shape of closed eyes or opened eyes. In the above method, wherein the combining is performed by using a first material image which includes at least a portion of the main image and a second material image which is the auxiliary image. In the above method, the combining is performed by applying a preset predetermined weight to each of a pixel value of the first material image and a pixel value of the second material image and summing the pixel values. In the above method, the predetermined weight is determined based on brightness of the second material image. In the above method, the combining comprises performing a reversal processing on a pixel value of the combined image or a pixel value of the combined image which is increased with respect to pixels of the first material image whose pixel value is substantially equal to or less than a preset reference value.

In the above method, the combining comprises selecting one of a pixel value of the first material image and a pixel value of the second material image with respect to each pixel of the combined image. In the above method, the combining comprises: quantizing the second material image; and selecting a pixel value of the second material image with respect to pixels having a preset quantized value and selecting a pixel value of the first material image with respect to the other pixels of the second material image. In the above method, the combining comprises: processing the second material image to emphasize contrast thereof; and selecting a pixel value of the first material image with respect to pixels that exceed a preset pixel value and selecting a pixel value of the second material image with respect to the other pixels of the second material image.

In the above method, the combining is performed by changing a pixel value of each pixel of the first material image based on a pixel value of the second material image. In the above method, the combining comprises at least partially overlapping the second material image on the first material image, and wherein a transparency of each pixel of the second material image is determined based on a pixel value of the second material image. In the above method, the combining is performed such that a variation in a pixel value of the first area before and after the combined image is displayed in the first area corresponds to a just noticeable difference (JND). In the above method, the position of the first area is randomly determined. In the above method, the combining and the displaying are repeated every time when a preset limit time elapses. In the above method, the preset limit time varies as the combining and the displaying are repeated. In the above method, as the combining and the displaying are repeated, the auxiliary image alternately displays closed eyes and opened eyes.

Another aspect is an apparatus for displaying an image, the apparatus comprising: an image generator configured to generate an auxiliary image configured to induce eye blinking of a user; and a display controller configured to i) display a main image in a display area, ii) combine the main image and the auxiliary image and iii) display the combined image in a first area corresponding to a portion of the display area. In the above apparatus, the auxiliary image is the shape of closed eyes or opened eyes.

Another aspect is a non-transitory computer readable recording medium having stored thereon code that when executed performs a method of displaying an image, the method comprising: displaying a main image in a display area of a display device; generating an auxiliary image configured to induce eye blinking of a user; combining the main image and the auxiliary image; and displaying the combined image in a first area corresponding to a portion of the display area.

In the above medium, the auxiliary image is the shape of closed eyes or opened eyes.

DETAILED DESCRIPTION OF CERTAIN INVENTIVE EMBODIMENTS

Reference will now be made in detail to embodiments, examples of which are illustrated in the accompanying drawings, wherein like reference numerals refer to like elements throughout and repeated description thereof will be omitted. Expressions such as "at least one of," when preceding a list of elements, modify the entire list of elements and do not modify the individual elements of the list.

It will be understood that although the terms "first", "second", etc. may be used herein to describe various components, these components should not be limited by these terms. These components are only used to distinguish one component from another. Singular expressions, unless defined otherwise in contexts, include plural expressions. In the embodiments below, it will be further understood that the terms "comprise" and/or "have" used herein specify the presence of stated features or components, but do not preclude the presence or addition of one or more other features or components.

In this disclosure, the term "substantially" includes the meanings of completely, almost completely or to any significant degree under some applications and in accordance with those skilled in the art. Moreover, "formed on" can also mean "formed over." The term "connected" includes an electrical connection.

Figure 1:
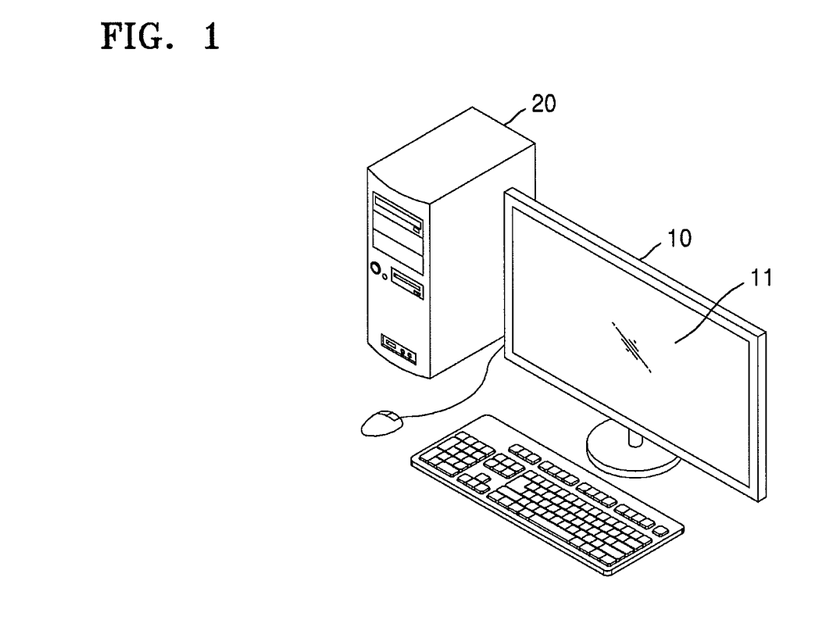
FIG. 1 illustrates a display apparatus according to an embodiment.

FIG. 1 illustrates a display apparatus according to an embodiment. Referring to FIG. 1, the display apparatus includes a display unit 10 and a computer 20 that controls the display unit 10. The display unit 10 includes a display area 11. Hereinafter, a method in which the computer 20 controls the display unit 10 will be described in detail.

Figure 2:
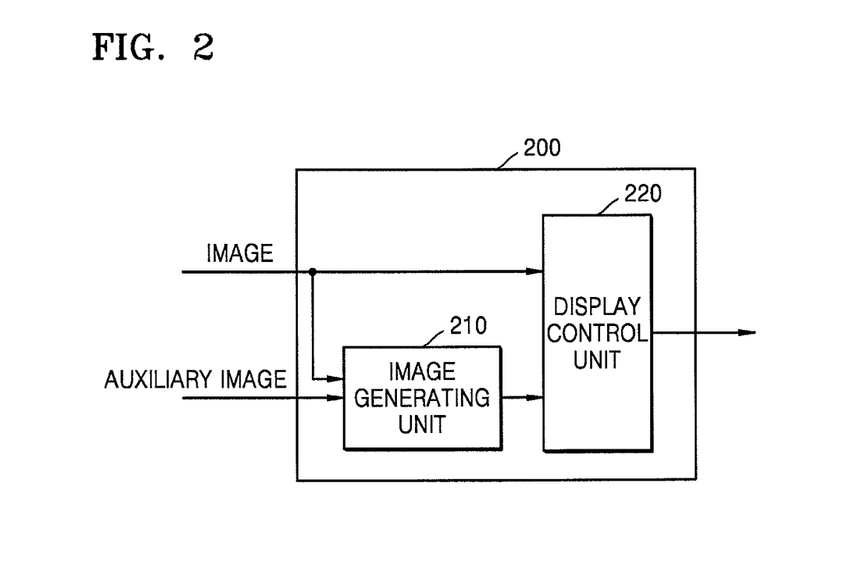
FIG. 2 is a structural diagram of a display control apparatus according to an embodiment.

FIG. 2 is a structural diagram of a display control apparatus 200 according to an embodiment. The display control apparatus 200 illustrated in FIG. 2 may be included in the computer 20 of FIG. 1. The display control apparatus 200 according to an embodiment controls an image displayed on the display unit 10. When a user looks at the display unit 10 for a long time, the number of eye blinks is reduced more than usual so that the dry eye syndrome is caused. In some embodiments, the display control apparatus 200 displays an image that may induce eye blinking of the user who looks at the display unit 10 in order to prevent occurrence of the dry eye syndrome. The displayed image may have the shape of the human eyes or shown eye blinking in order to induce unconscious eye blinking of the user when the user looks at the displayed image.

The display control apparatus 200 illustrated in FIG. 2 includes only components related to the present embodiment not to obscure the main characteristics thereof. Accordingly, other general-use components may be further included in addition to the components illustrated in FIG. 2.

The display control apparatus 200 may correspond to or include at least one processor. Accordingly, the display control apparatus 200 may be included in a microprocessor or other hardware device such as a general-use computer system and driven therein.

Referring to FIG. 2, the display control apparatus 200 includes an image generating unit or an image generator 210 and a display control unit or a display controller 220.

The image generating unit 210 generates an image that induces eye blinking by using an image displayed on the display unit 10 (hereinafter, 'a background image') and an auxiliary image that is provided to generate the image that induces eye blinking. The auxiliary image may be in the shape of human eyes. For example, the auxiliary image may be a still image showing closed human eyes or opened human eyes or a moving image that shows eye blinking.

When a first area that displays the image that induces eye blinking is determined, the image generating unit 210 may generate the image that induces eye blinking by using a first material image that is included in the first area of the background image and a second material image which is the auxiliary image. For example, the image generating unit 210 may generate the image that induces eye blinking by deforming the first material image by referring to the second material image.

The image generating unit 210 may generate the image that induces eye blinking by combining the first and second material images. For example, the image that induces eye blinking may be generated by calculating an average of pixel values of the first and second material images and setting the average as a pixel value of the image that induces eye blinking. When calculating the average of the pixel values of the first and second material images, an average calculation algorithm may be used by applying a parameter or a weight. The parameter or the weight may be determined according to characteristics of the first and second material images. The characteristics of the first and second material images may be related to, for example, brightness, luminance, or chromacity, that is, a pixel value, but are not limited thereto. For example, if the second material image is too bright or too dark, a small weight may be applied to the second material image so that the pixel value of the second material image is reflected in the image that induces eye blinking by a relatively small ratio.

The image generating unit 210 may generate the image that induces eye blinking by overlapping the second material image on the first material image. The second material image may have a predetermined transparency. All pixels of the second material image may have the same predetermined transparency or different transparencies. The image generating unit 210 may determine a transparency of each pixel according to a pixel value of each pixel of the second material image. For example, the image generating unit 210 may set a higher transparency to a pixel if the pixel value of each pixel of the second material image is higher, that is, if the luminance of the second material image is higher. If the color of eyebrows and eyes of the user displayed on the second material image is dark and thus a pixel value of a corresponding pixel is assumed to be low, the image generating unit 210 may set a low transparency or a first transparency to a portion of the second material image corresponding to the eyebrows and eyes and a high transparency or a second transparency higher than the first transparency to the other portion so as to generate an image that induces eye blinking wherein the eyebrows and the eyes are clearly distinguished. On the contrary, if the color of the eyebrows and eyes of the user displayed on the second material image is bright and thus a pixel value of a corresponding pixel is assumed to be high, the image generating unit 210 may set a high transparency to a portion of the second material image corresponding to the eyebrows and eyes and a low transparency to the other portion. As such, the eyebrows and the eyes are clearly distinguished in the second material image compared to the first material image.

The image generating unit 210 may generate the image that induces eye blinking such that visibility of the generated image the induces eye blinking compared to a background image is higher, for example, by performing a reversal processing on the generated image that induces eye blinking according to a pixel value of the background image or correcting a pixel value of the generated image that induces eye blinking.

The image generating unit 210 may generate the image that induces eye blinking by selecting one of pixel values of the first and second material images as a pixel value of each pixel of the image that induces eye blinking. The criterion for selecting a pixel value may be the pixel value of the second material image.

The image generating unit 210 may generate the image that induces eye blinking by deforming the first material image based on the pixel value of the second material image. For example, the image that induces eye blinking is generated by setting a relatively low pixel value to the first material image with respect to pixels of the second material image having a pixel value that is substantially equal to or lower than a predetermined reference value. If the second material image is an image showing the human eyes, a portion of the second material image whose pixel value is substantially equal to a predetermined reference or lower may be assumed to be eyebrows or eyelashes, and by lowering a pixel value of the same portion of the first material image and using the portion as the image that induces eye blinking, the shape of the eyebrows or eyelashes may be perceived in the image that induces eye blinking.

The image generating unit 210 may generate the image that induces eye blinking such that a degree in a variation of a screen of the first area before and after displaying the image that induces eye blinking in the first area corresponds to a just noticeable difference (JND). The JND refers to a minimum difference required to identify that two stimuli different from each other and is expressed as a relative ratio with respect to a reference stimulus. According to various researches, human's eyesight may perceive a change of about 8% with respect to a reference stimulus. Thus, the image generating unit 210 may generate the image that induces eye blinking such that brightness of the first area after the image that induces eye blinking is displayed in the first area is changed by about 8% or above compared to the brightness of the image that induces eye blinking before being displayed. According to the above, when the image that induces eye blinking is displayed, the user may perceive the same. Also, when the image that induces eye blinking is generated such that the brightness of the first area after the image that induces eye blinking is displayed in the first area is changed by about 8% compared to the brightness before the image that induces eye blinking is displayed, eye blinking of the user may be induced, and at the same time, the user would not feel awkward or any inconvenience due to an excessive change on the screen.

Detailed examples of the embodiments in which the image that induces eye blinking is generated will be additionally described with reference to FIGS. 4 through 8.

According to an embodiment, the display control unit 220 displays the image that induces eye blinking and is generated by the image generating unit 210 in the first area of the display unit 10. The first area may be a portion of the entire display area of the display unit 10, and thus, a probability that the user sees the image that induces eye blinking is further increased. The first area may be preset to be a predetermined position or may be randomly located. By randomly setting a position of the first area, predictability that a user may predict a position of the first area may be reduced and the effect of inducing eye blinking may be increased.

According to an embodiment, the display control unit 220 may repeatedly display the image that induces eye blinking in the first area every time when a preset limit time elapses. The image that induces eye blinking may be the same despite repeated displaying, or a new image that induces eye blinking may be reproduced every time when displaying is repeated. In this case, the image generating unit 210 may generate a new image that induces eye blinking every time when the preset limit time elapses. The limit time may be fixed or may vary as a user status is recognized, or may be set such that it is gradually reduced or increased according to a preset method. When an image that induces eye blinking is repeatedly displayed, at least two types of the image that induces eye blinking may be alternately displayed. At least two types of second material images may be alternately used to generate an image that induces eye blinking. For example, a second material image showing closed eyes and a second material image showing opened eyes may be alternately used, or an image that induces eye blinking showing closed eyes and an image that induces eye blinking showing opened eyes may be alternately displayed. The limit time may be based on a number of frames or based on time. The limit time may correspond to at least five frames.

The display control unit 220 may display an image that induces eye blinking in the first area also when a predetermined event is generated. When the image that induces eye blinking is generated regardless of a background image, the display control unit 220 may display the previously generated image that induces eye blinking every time when the event is generated. However, when the image that induces eye blinking is based on the background image, the image generating unit 210 may generate an image that induces eye blinking, and the display control unit 220 may display the generated image that induces eye blinking in the first area. The event may be generated when, for example, eye blinking of the user is not sensed during a preset critical time period.

Figure 3:
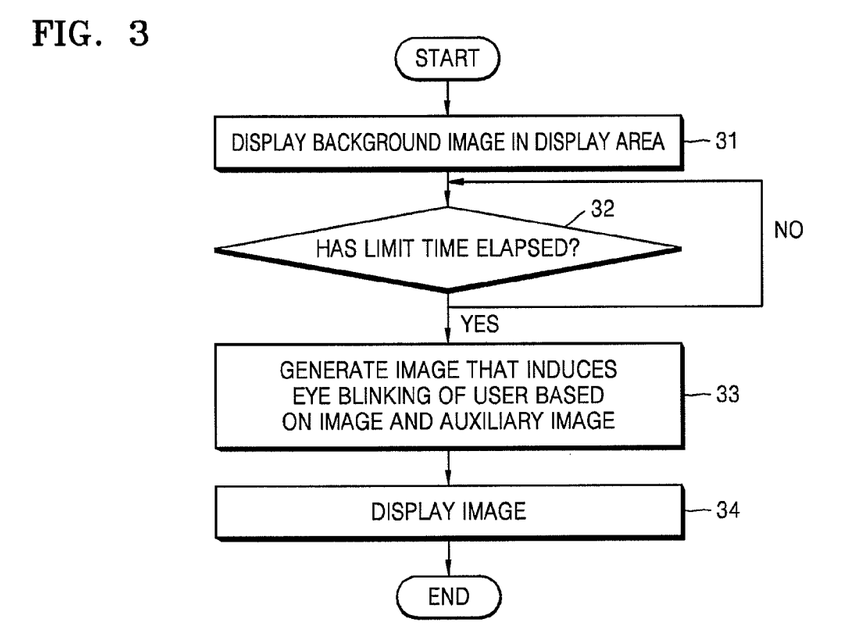
FIG. 3 is a flowchart of a display control method according to an embodiment.

FIG. 3 is a flowchart of a display control method according to an embodiment. In some embodiments, the FIG. 3 procedure is implemented in a conventional programming language, such as C or C++ or another suitable programming language. The program can be stored on a computer accessible storage medium of the display control apparatus 200, for example, a memory (not shown) of the display control apparatus 200. In certain embodiments, the storage medium includes a random access memory (RAM), hard disks, floppy disks, digital video devices, compact discs, video discs, and/or other optical storage mediums, etc. The program can be stored in the processor. The processor can have a configuration based on, for example, i) an advanced RISC machine (ARM) microcontroller and ii) Intel Corporation's microprocessors (e.g., the Pentium family microprocessors).

In certain embodiments, the processor is implemented with a variety of computer platforms using a single chip or multichip microprocessors, digital signal processors, embedded microprocessors, microcontrollers, etc. In another embodiment, the processor is implemented with a wide range of operating systems such as Unix, Linux, Microsoft DOS, Microsoft Windows 8/7/Vista/2000/9x/ME/XP, Macintosh OS, OS X, OS/2, Android, iOS and the like. In another embodiment, at least part of the procedure can be implemented with embedded software. Depending on the embodiment, additional states can be added, others removed, or the order of the states changed in FIG. 3.

The display control method illustrated in FIG. 3 includes operations that are performed in time series in the display control apparatus 200 illustrated in FIG. 2. Thus, the descriptions provided above with reference to the elements illustrated in FIG. 2 also apply to the method illustrated in FIG. 3.

Referring to FIG. 3, in operation 31, the display control unit 220 of FIG. 2 displays a background image in the display area 11 of the display unit 10.

In operation 32, a timer (not shown) determines whether a preset limit time has elapsed. If it is determined that the limit time has elapsed, the timer may generate an event, and when the event is generated, the method proceeds to operation 33. The limit time may be set in units of time or frames, for example, in units of about 4 seconds or about 240 frames. However, if a screen changes repeatedly every time when the limit time elapses, and a too short limit time is set, the user may not recognize the change of the screen. Thus, when the limit time is in units of frames, the limit time may be set to at least five frames. Meanwhile, according to a modification example of operation 32, the timer may determine whether a preset event is generated. The event may be generated when eye blinking of the user has not been sensed at all until a predetermined critical time is elapsed.

In operation 33, the image generating unit 210 generates an image that induces eye blinking of the user based on the background image and an auxiliary image. The background image may be an image that is displayed on the entire display area 11 of the display unit 10, and the auxiliary image may be an image that is used to generate the image that induces eye blinking and is in the shape of human eyes.

In operation 34, the display control unit 220 displays the image that induces eye blinking generated in operation 33 in a first area which is a portion of the display area 11. The time for displaying the image that induces eye blinking in the first area may be very short. For example, the image that induces eye blinking may be displayed for one frame only. Thus, without excessively disturbing the user who is seeing the background image, eye blinking of the user may be induced by making the user see the image that induces eye blinking.

Meanwhile, operations 32 through 34 of FIG. 3 may be repeated. Every time when operations 32 through 34 are repeated, the limit time may be modified.

FIGS. 4 through 8 are views for explaining a method of generating an image that induces eye blinking according to embodiments. Hereinafter, various examples of generating an image that induces eye blinking according to embodiments will be described with reference to FIGS. 4 through 8.

Figure 4:
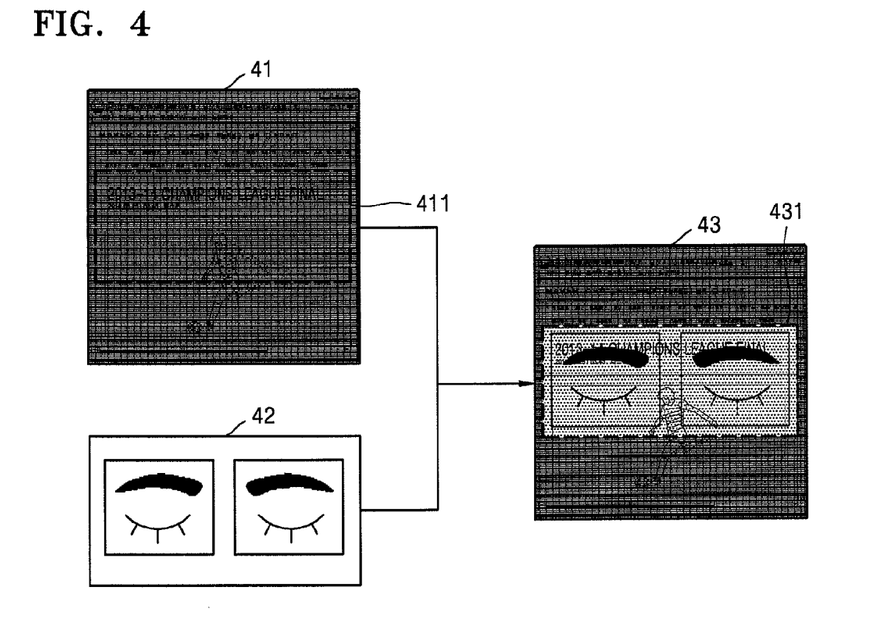
FIGS. 4 through 8 are views for explaining a method of generating an image that induces eye blinking of a user, according to embodiments.

First, referring to FIG. 4, the image generating unit 210 of FIG. 2 combines a background image 41 and an auxiliary image 42 to generate an image 431 that induces eye blinking. The display control unit 220 may display the image 431 together with the background image 41. A screen 43 displays a state in which the image 431 is displayed in a first area, which is a portion of the background image 41.

As can be seen from FIG. 4, the image generating unit 210 may use a typical average algorithm to generate the image 431. For example, the image 431 may be generated by calculating an average pixel value of each pixel of a first material image 411 included in the first area of the background image 41 and a second material image 42, which is an auxiliary image. To this end, Equation 1 below may be used.

$$(R, G, B) = \frac{(R1, G1, B1) + (R2, G2, B2)}{2}, \quad \text{Equation 1}$$

where (R, G, B) is a pixel value of the image 431, (R1, G1, B1) is a pixel value of the first material image 411, and (R2, G2, B2) is a pixel value of the second material image 42. The image generating unit 210 may apply Equation 1 on each pixel of the image 431 to generate the image 431.

Meanwhile, the image generating unit 210 may generate the image 431 by using Equation 2 in order to prevent the user from being disturbed too much when the image 431 is displayed on the screen.

$$(R, G, B) = \frac{(R1, G1, B1) + (R2, G2, B2) \times p}{2}, \quad 0 < p \le 1 \quad \text{Equation 2}$$

According to Equation 2, when a first material image and a second material image are averaged to generate an image that induces eye blinking or a user, a weight may be applied to the second material image. Here, p denotes a weight to be applied to the second material image. If p is 1, the first material image and the second material image are summed at the same ratio like in Equation 1, and as p decreases, the second material image is summed at a lower ratio than the first material image. A degree of using the second material image to generate the image that induces eye blinking varies with the value of p. Thus, if it is not desired that the user excessively perceive the image that induces eye blinking, a small p may be set, and if quick eye blinking of the user is desired, a great p may be set so that an image that induces eye blinking may be differently generated according to a desired purpose. The value of p may be differently determined according to characteristics of the second material image. For example, if the second image is too bright or too dark, a small p may be set so that the image that induces eye blinking may be naturally recognized by the user when it is displayed on the screen.

Figure 5:
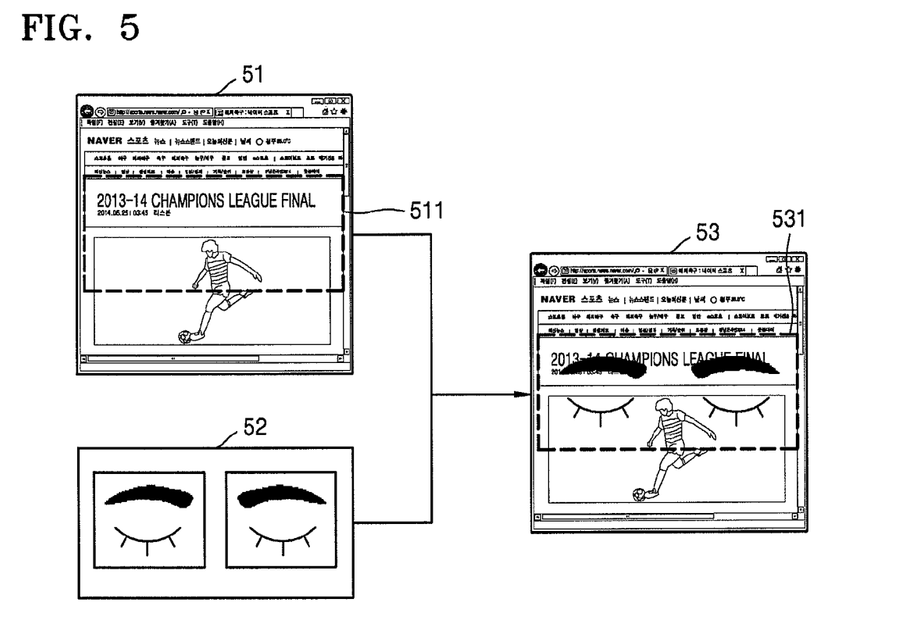

Next, referring to FIG. 5, the image generating unit 210 of FIG. 2 may generate an image 531 that induces eye blinking by combining a background image 51 and an auxiliary image 52. The display control unit 220 may display the image 531 along with the background image 51. The screen 53 illustrates a state in which the image 531 is displayed in a first area which is a portion of the background image 51.

The image generating unit 210 may generate the image 531 by at least partially overlapping a first material image 511 corresponding to the first area of the background image 51 and a second material image 52 which is an auxiliary image. The image generating unit 210 may display the second material image 52 by at least partially overlapping the same on the first material image 511, and the second material image 52 that is at least partially overlapped may have a predetermined transparency. Thus, a portion of the first material image 511 that is at least partially overlapped behind the second material image 52 may be included in the image 531.

The second material image 52 may have substantially uniform transparency or respective pixels of the second image 52 may have different transparencies. Regarding the image 531 illustrated in FIG. 5, for example, a transparency of a portion of the second material image 52 corresponding to the eyebrows and eyes is about 0%, and a transparency of the other portion of the second image 52 is about 100%. The portion of the second material image 52 corresponding to the eyebrows and eyes may be recognized according to its shape through image processing but the disclosed embodiments are not limited thereto, and the portion may be recognized according to a user setting, pixels, or edge detection.

For example, the image generating unit 210 may generate the image 531 by quantizing a pixel value of the second material image 52 to 0 (black) or 1 (white), and setting a predetermined value, for example, a transparency of a pixel corresponding to 1, to 100% and a transparency of the other pixels to 0%, and then displaying the second material image 52 by overlapping the same on the first material image 511.

Alternatively, the image generating unit 210 may generate the image 531 by quantizing a pixel value of the second material image 52 to 0 (black) or 1 (white), and considering a pixel value of 1 as a pixel value of the first material image 511 and a pixel value of 0 as a pixel value of the second material image 52.

Instead of quantizing the pixel value of the second material image 52 to 1 bit, the image generating unit 210 may convert the same to two or three bits, and in this case, the above-described embodiment may be modified. The numerical value of the transparency described above is exemplary, and thus the embodiments of the present invention are not limited thereto.

According to the above-described embodiment, the image generating unit 210 generates the image 531 that induces eye blinking by using the background image 51, which is an original image, without any change except for a portion corresponding to the eyebrows and eyes, or by increasing a ratio of the background image 51, and thus, a sense of frustration or unpleasantness that the user may feel may be reduced.

Figure 6:
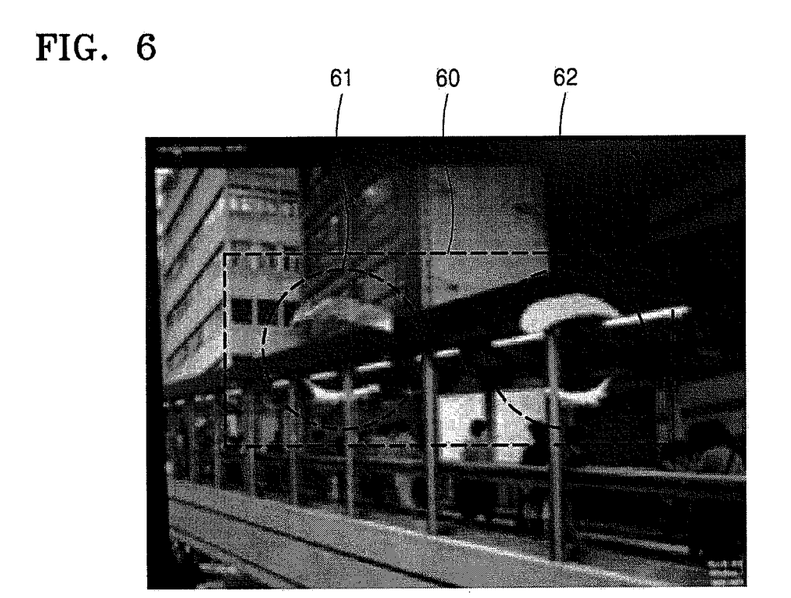

Next, referring to FIG. 6, the image generating unit 210 may perform a reversal processing on a portion of an image 60 that induces eye blinking or generate portions of the image 60 by using different methods.

According to an embodiment, the image generating unit 210 may first generate a first image that induces eye blinking according to the above-described methods. Next, the image generating unit 210 may correct the first image that induces eye blinking according to a pixel value of a first material image corresponding to a first area on which the image 60 is displayed, to thereby finally generate the image 60. For example, the image generating unit 210 may generate first a first image that induces eye blinking according to the above-described methods, and then may perform a reversal processing on a portion of the first image that induces eye blinking with respect to an area of the first material image whose pixel value is equal to or less than a predetermined critical value.

FIG. 6 illustrates that only a portion of the second material image corresponding to eyes is displayed on the background image and the other portion of the second material image is processed be become transparent via the quantization method and transparencies applied according to a result of quantization are applied. Referring to FIG. 6, a left eye 61 and a right eye 62 are illustrated, and a pixel value of the background image overlapped on the left eye 61 is lower than a pixel value of the background image overlapped on the right eye 62. The image generating unit 210 may process a portion of the overlapped background image corresponding to the right eye 62 and having a lower pixel value to be brighter or may perform a reversal processing on the portion corresponding to the right eye 62 so as to increase a visibility with respect to a dark background.

The eyes are likely to be displayed in a darker color than a skin color in the second material image, and if a pixel value of the first material image which is the background of the eyes is equal to or less than a critical value, the eyebrows, the eyes, and the background are all dark, and thus, the eyebrows and the eyes may not be easily seen. In this case, a reversal processing may be performed on a portion of the first material image whose pixel value is substantially equal to or less than a critical value and which corresponds to the eyes of the first image that induces eye blinking or the pixel value of the first material image may be increased so that the portion corresponding to the eyes may become bright. Accordingly, the visibility of the image that induces eye blinking may be improved, and also the visibility of the image that induces eye blinking may be uniformly adjusted over the entire area thereof.

As a standard for determining a portion of the first image that induces eye blinking and to which a reversal processing or readjustment of a pixel value is to be performed, whether to determine the pixel value of the first material image is substantially equal to or less than a critical value has been described above. However, the disclosed embodiments are not limited thereto. For example, a final image that induces eye blinking may be generated by dividing the pixel value of the first material image into a plurality of sections, and performing different processings on respective pixels according to which section the pixel value of the first material image corresponding to each pixel of the first material image in the first image that induces eye blinking corresponds. Accordingly, processings on the image that induces eye blinking vary according to a pixel value of the first material image which is the background, and visibility of the final image that induces eye blinking is substantially uniformly adjusted over the entire area thereof.

Figure 7:
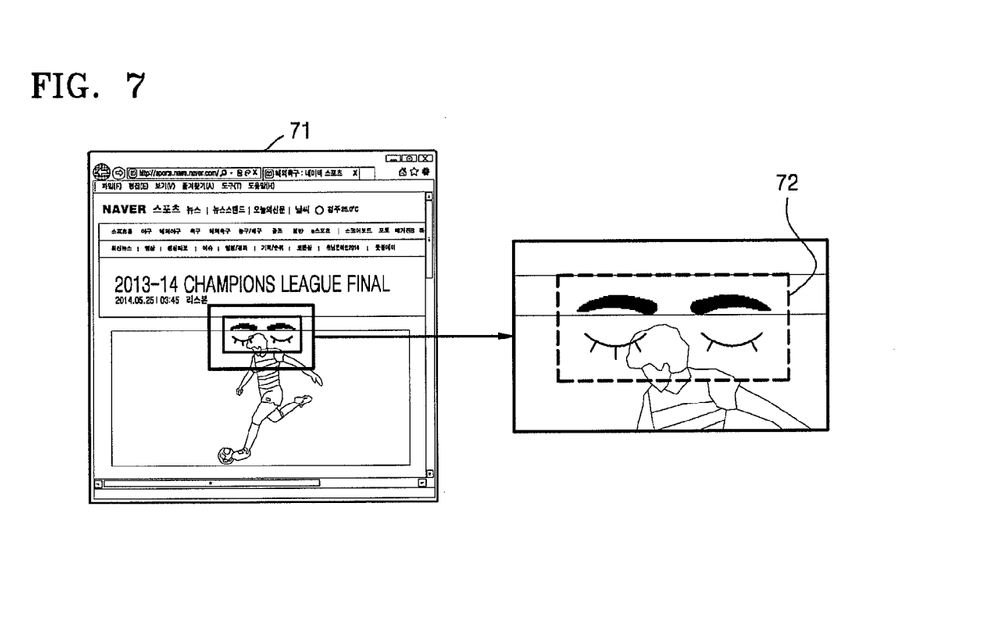

Next, referring to FIG. 7, the image generating unit 210 may generate an image 72 that induces eye blinking having a size of about 1% or less with respect to a background image 71, and the display control unit 220 may display the image 72 in a center of the background image 71. The ratio may be about 1% or less with respect to the background image 71. However, when an image that induces eye blinking having a size that is about 1% or less with respect to a background image is generated, the image that induces eye blinking may be generated by using only a second material image. Based on the basic assumption that the image that induces eye blinking does not considerably disturb the eyes of a user as the size thereof is small, instead of generating a natural image that induces eye blinking by combining the second material image with a background image, an auxiliary image that may induce clear eye blinking effects is used. It has been experimentally determined that, when an image that induces eye blinking having an area of 0.3% with respect to a background image is generated by using only a second material image and displayed in a center of the background image 71, eye blinking of the user increases by more than by 10%.

Figure 8:
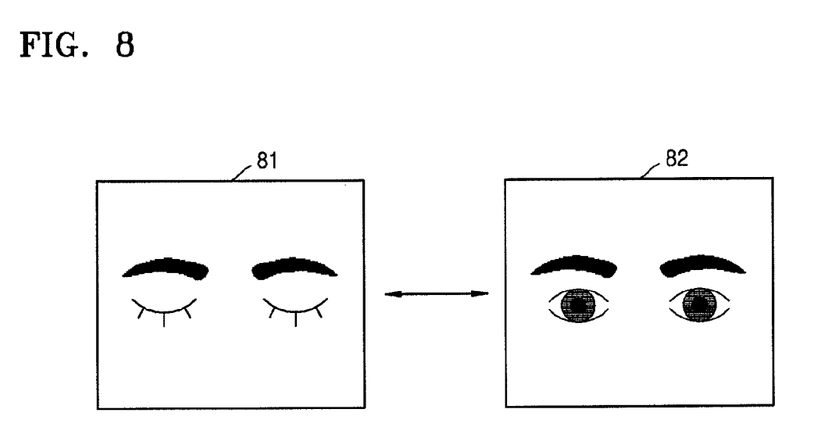

Finally, referring to FIG. 8, the image generating unit 210 may alternately use a first auxiliary image 81 showing closed eyes and a second auxiliary image 82 showing opened eyes as the auxiliary image used to generate the image that induces eye blinking. The display control unit 220 may further effectively induce eye blinking of the user by alternately displaying a first material image that induces eye blinking generated by using the first auxiliary image 81 and a second material image that induces eye blinking generated by using the second auxiliary image 82. For example, the display control unit 220 may alternately display the first material image that induces eye blinking and the second material image that induces eye blinking every time when an event is generated. Alternately, the display control unit 220 may continuously display the first material image that induces eye blinking and the second the image that induces eye blinking at a predetermined interval every time when an event is generated. That is, every time when an event is generated, an image showing closed eyes and an image showing opened eyes may be continuously displayed. The predetermined interval may be, for example, five frames. The event may be generated by using various methods such as, by using a timer, a processor or a sensor.

As described above, according to at least one of the above embodiments, eye blinking of the user is inducted to thereby reduce a probability of dry eye syndrome.

It should be understood that the exemplary embodiments described therein should be considered in a descriptive sense only and not for purposes of limitation. Descriptions of features or aspects within each embodiment should typically be considered as available for other similar features or aspects in other embodiments.

While the inventive technology has been described with reference to the figures, it will be understood by those of ordinary skill in the art that various changes in form and details may be made therein without departing from the spirit and scope of the present invention as defined by the following claims.

What is claimed is:

1. A method of displaying an image, the method being performed by a processor and comprising:
    displaying a main image in a display area of a display device;
    generating, at an image generator, an auxiliary image configured to induce eye blinking of a user;
    combining, at a display controller, the main image and the auxiliary image; and
    displaying, at the display device, the combined image in a first area corresponding to a portion of the display area,
    wherein the position of the first area varies periodically by randomly determining the position of the first area and setting a time limit,
    wherein the combining is performed by using a first material image which includes at least a portion of the main image and a second material image which is the auxiliary image, wherein the combining comprises at least partially overlapping the second material image on the first material image, wherein a transparency of each pixel of the second material image is determined based on a pixel value of the second material image,
    wherein when pixel values of a first portion of the second material image are lower than pixel values of a second portion of the second material image, a first transparency is set to the first portion of the second material image and a second transparency higher than the first transparency is set to the second portion of the second material image,
    wherein when the pixel values of the first portion of the second material image are higher than the pixel values of the second portion of the second material image, the second transparency is set to the first portion of the second material image and the first transparency is set to the second portion of the second material image, and
    wherein the combining is performed by applying a preset predetermined weight to the pixel value of the second material image to generate a weighted pixel value and averaging a sum of the weighted pixel value and a pixel value of the first material image.

2. The method of claim 1, wherein the auxiliary image has a shape of closed eyes or opened eyes.

3. The method of claim 1, wherein the predetermined weight is determined based on brightness of the second material image.

4. The method of claim 1, further comprising correcting the combined image by performing a reversal processing on pixel values of pixels of a first portion of the combined image or increasing pixel values of the pixels of the first portion of the combined image, when pixel values of pixels of the first material image corresponding to the first area are equal to or less than a preset reference value.

5. The method of claim 1, wherein the combining is performed such that a variation in a pixel value of the first area before and after the combined image is displayed in the first area corresponds to a just noticeable difference (JND).

6. The method of claim 1, wherein the combining and the displaying are repeated every time when the time limit elapses.

7. The method of claim 1, wherein the time limit varies as the combining and the displaying are repeated.

8. The method of claim 1, wherein as the combining and the displaying are repeated, the auxiliary image alternately displays closed eyes and opened eyes.

9. The method of claim 1, wherein the first portion of the second material image comprises shapes of eyebrows and eyes, the method further comprising, when a color of the shapes of the eyebrows and the eyes of the second material image is darker than the second portion of the second material image, setting, at the image generator, the first transparency to the first portion of the second material image and the second transparency to the second portion so as to generate an image that induces eye blinking such that the shapes of the eyebrows and the eyes are clearly distinguished.

10. The method of claim 1, wherein the first portion of the second material image comprises shapes of eyebrows and eyes, the method further comprising, when a color of the shapes of the eyebrows and the eyes of the second material image is brighter than the second portion of the second material image, setting, at the image generator, the second transparency to the first portion and the first transparency to the second portion so as to generate an image that induces eye blinking such that the shapes of the eyebrows and the eyes are clearly distinguished.

11. An apparatus for displaying an image, the apparatus comprising:
    an image generator configured to generate an auxiliary image configured to induce eye blinking of a user; and
    a display controller configured to i) display a main image in a display area, ii) combine the main image and the auxiliary image and iii) display the combined image in a first area corresponding to a portion of the display area, wherein the auxiliary image has a smaller displayable area than the main image, wherein the position of the first area varies periodically by randomly determining the position of the first area and setting a time limit, wherein the display controller is configured combine by using a first material image which includes at least a portion of the main image and a second material image which is the auxiliary image, wherein the combining comprises at least partially overlapping the second material image on the first material image, wherein a transparency of each pixel of the second material image is determined based on a pixel value of the second material image, wherein when pixel values of a first portion of the second material image are lower than pixel values of a second portion of the second material image, a first transparency is set to the first portion of the second material image and a second transparency higher than the first transparency is set to the second portion of the second material image, wherein when pixel values of the first portion of the second material image are higher than pixel values of the second portion of the second material image, the second transparency is set to the first portion of the second material image and the first transparency is set to the second portion of the second material image, and wherein the display controller is configured to perform the combining by applying a preset predetermined weight to the pixel value of the second material image to generate a weighted pixel value and averaging a sum of the weighted pixel value and a pixel value of the first material image.

12. The apparatus of claim 11, wherein the auxiliary image has a shape of closed eyes or opened eyes.

13. A non-transitory computer readable recording medium having stored thereon code that when executed performs a method of displaying an image, the method comprising:

displaying a main image in a display area of a display device;

generating, at an image generator, an auxiliary image configured to induce eye blinking of a user;

combining, at a display controller, the main image and the auxiliary image; and displaying, at the display device, the combined image in a first area corresponding to a portion of the display area, wherein the position of the first area varies periodically by randomly determining the position of the first area and setting a time limits wherein the combining is performed by using a first material image which includes at least a portion of the main image and a second material image which is the auxiliary image, wherein the combining comprises at least partially overlapping the second material image on the first material image, wherein a transparency of each pixel of the second material image is determined based on a pixel value of the second material image, wherein when pixel values of a first portion of the second material image are lower than pixel values of a second portion of the second material image, a first transparency is set to the first portion of the second material image and a second transparency higher than the first transparency is set to the second portion of the second material image, wherein when pixel values of the first portion of the second material image are higher than pixel values of the second portion of the second material image, the second transparency is set to the first portion of the second material image and the first transparency is set to the second portion of the second material image, and wherein the combining is performed by applying a preset predetermined weight to the pixel value of the second material image to generate a weighted pixel value and averaging a sum of the weighted pixel value and a pixel value of the first material image.

14. The medium of claim 13, wherein the auxiliary image is a shape of closed eyes or opened eyes.

* * * * *